United States Patent [19]

Iba et al.

[11] Patent Number: 5,143,104
[45] Date of Patent: Sep. 1, 1992

[54] VENTED APPARATUS FOR STORING AND CLEANING AN ELEMENT

[75] Inventors: Wayne S. Iba, Mission Viejo; Gregory R. Holland, Irvine; Alix A. Moore, Santa Ana; Walter A. York, Mission Viejo, all of Calif.

[73] Assignee: Allergan, Inc., Irvine, Calif.

[21] Appl. No.: 624,057

[22] Filed: Dec. 7, 1990

[51] Int. Cl.⁵ .............................................. B08B 3/04
[52] U.S. Cl. ................... 134/135; 134/200; 134/201
[58] Field of Search ............... 134/135, 201, 92, 137, 134/901, 200

[56] References Cited

U.S. PATENT DOCUMENTS

| | | | |
|---|---|---|---|
| 3,063,083 | 11/1962 | Obitts | 134/901 |
| 4,002,234 | 1/1977 | Loshaek | 134/137 |
| 4,396,583 | 8/1983 | LeBoeuf | 134/901 |
| 4,750,610 | 6/1988 | Ryder | 134/901 |
| 4,889,693 | 12/1989 | Su et al. | 134/901 |

Primary Examiner—Frankie L. Stinson
Attorney, Agent, or Firm—Poms, Smith, Lande & Rose

[57] ABSTRACT

An apparatus for storing and cleaning an element is disclosed. The apparatus includes a fluid containing receptacle having an open top and a cap having at least one opening therethrough for removably closing off the open top of the receptacle. The apparatus further includes an element retaining housing removably disposed internally of said receptacle. The housing has at least one opening therethrough fluidly communicating the interior of the housing with the exterior thereof. The apparatus also includes a resilient gasket mounted in the receptacle adjacent the opening in the cap. The gasket has normally closed valving means therein adapted to open upon a predetermined increase in pressure within said receptacle to release the pressure through said valving means and out of said opening in said cap.

11 Claims, 4 Drawing Sheets

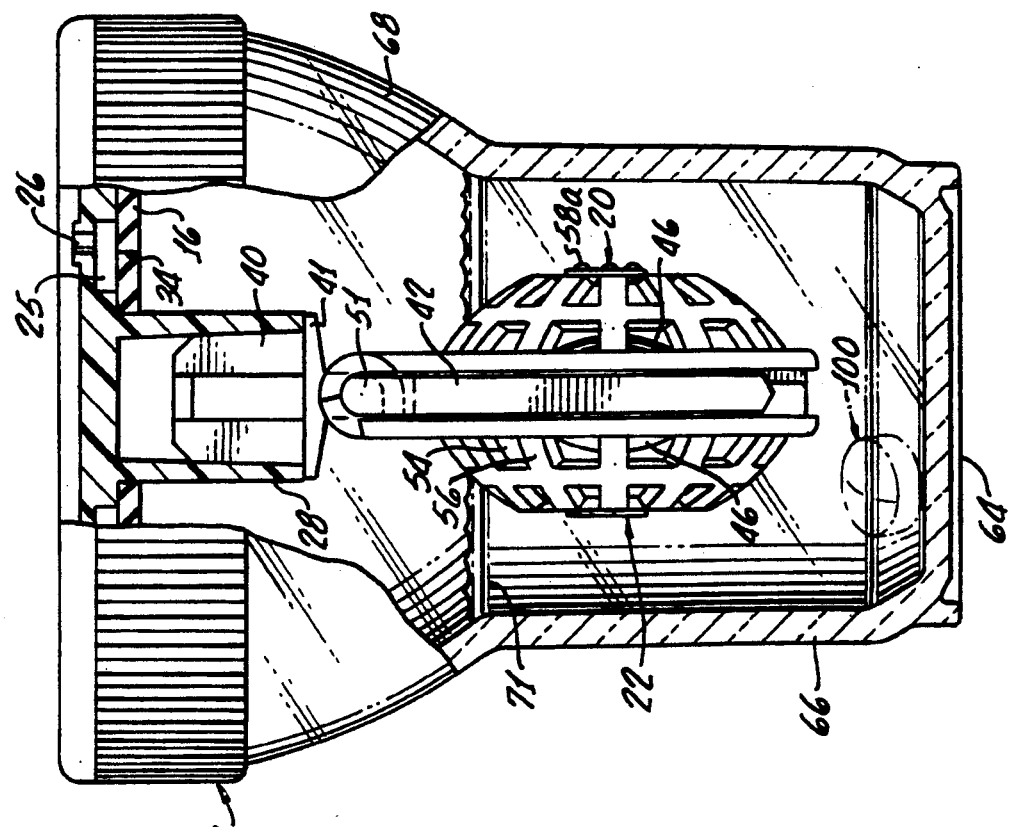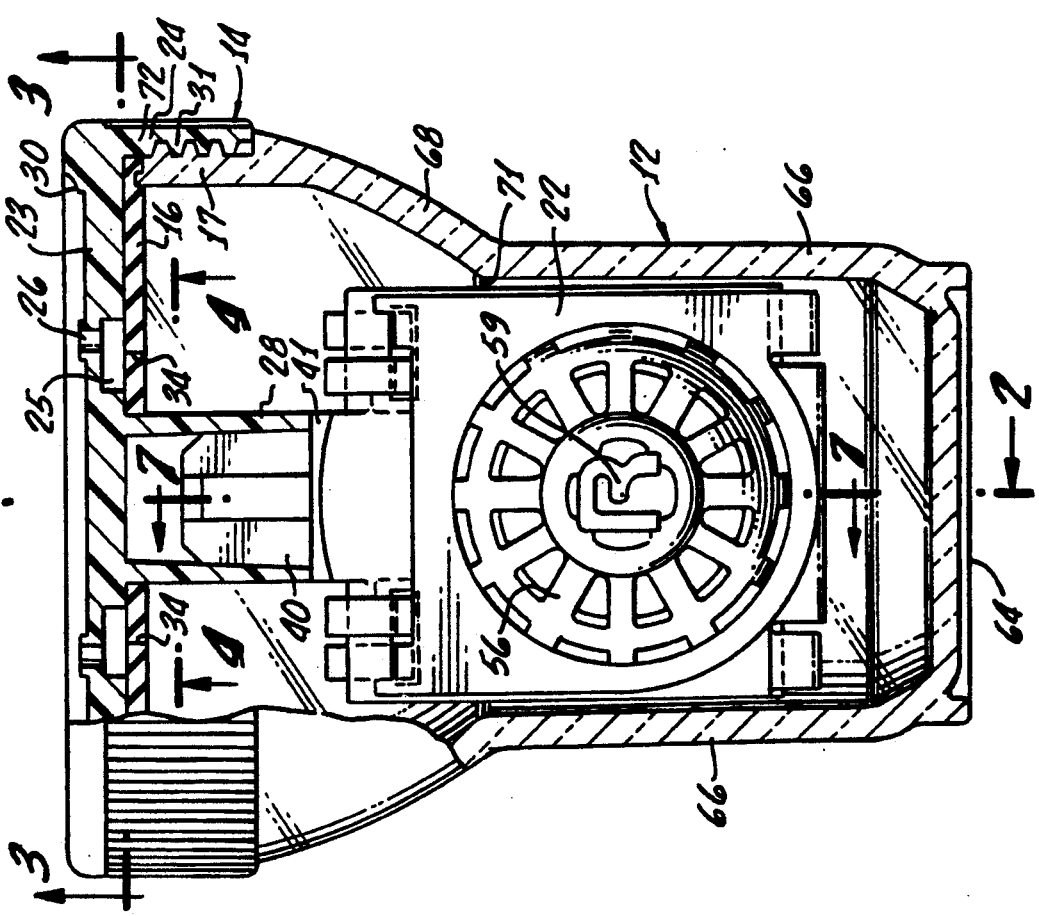

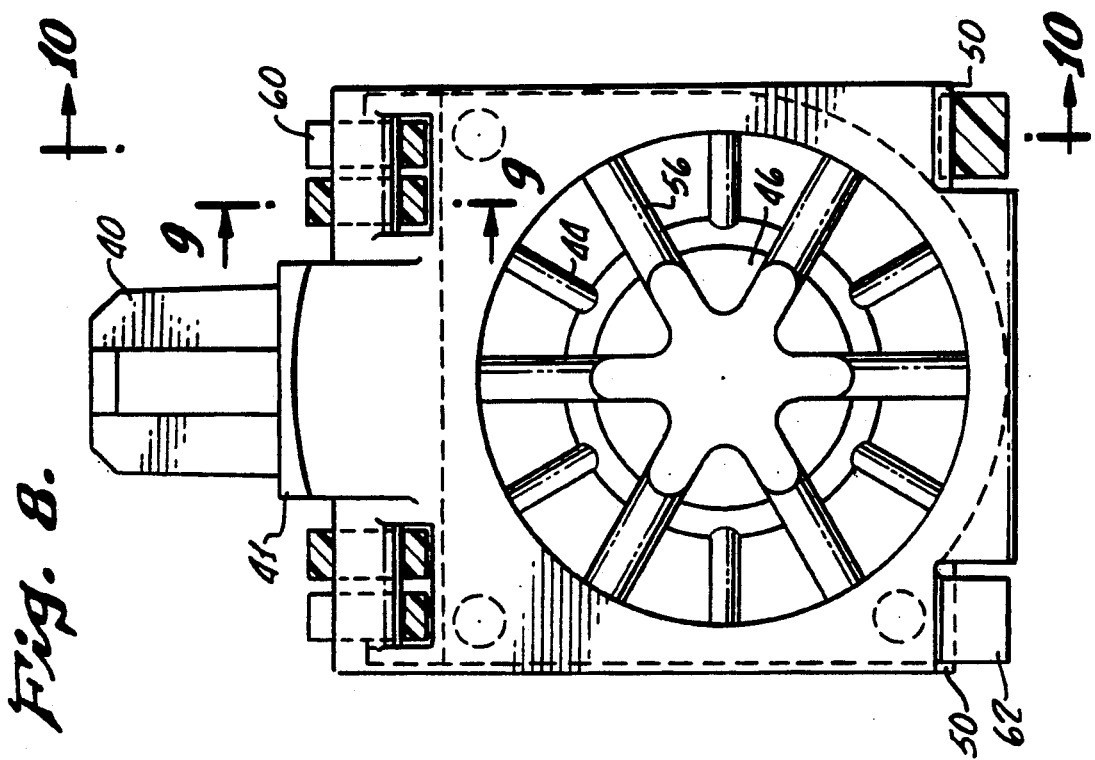
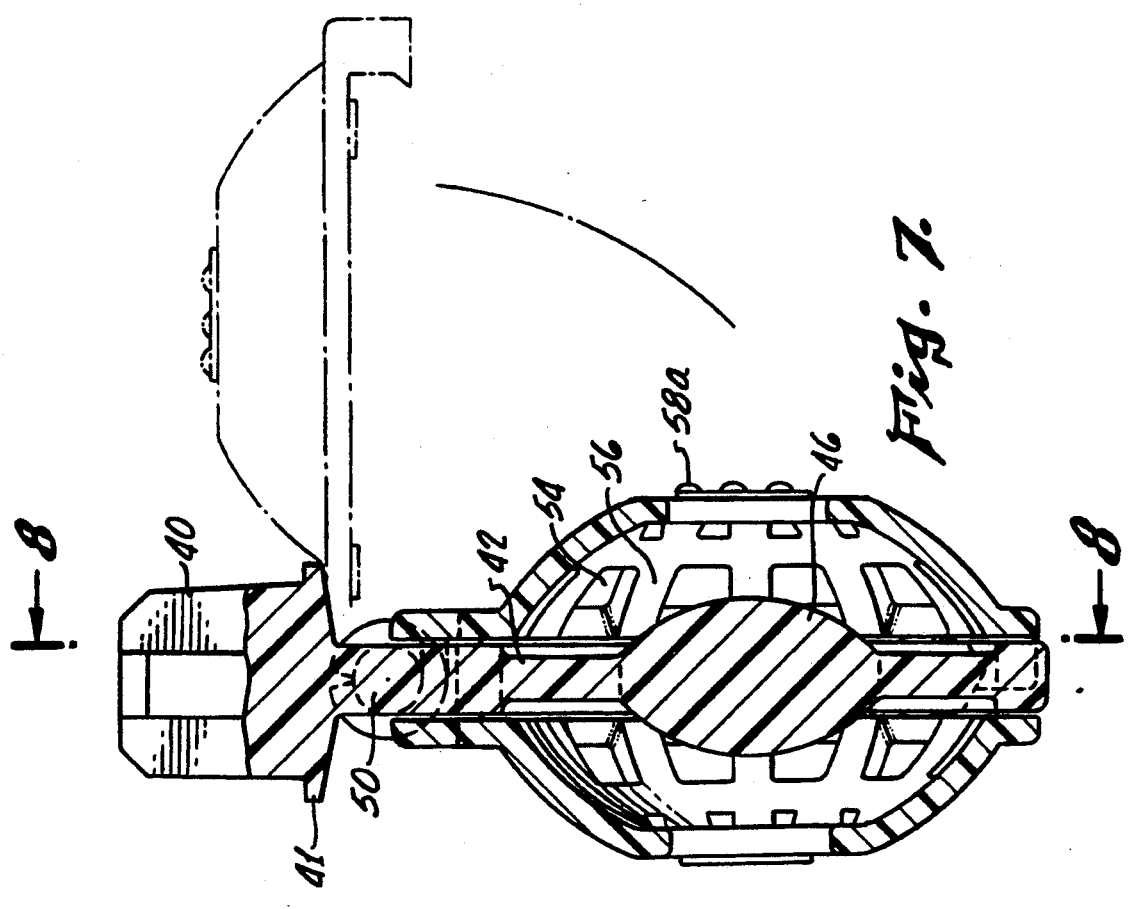

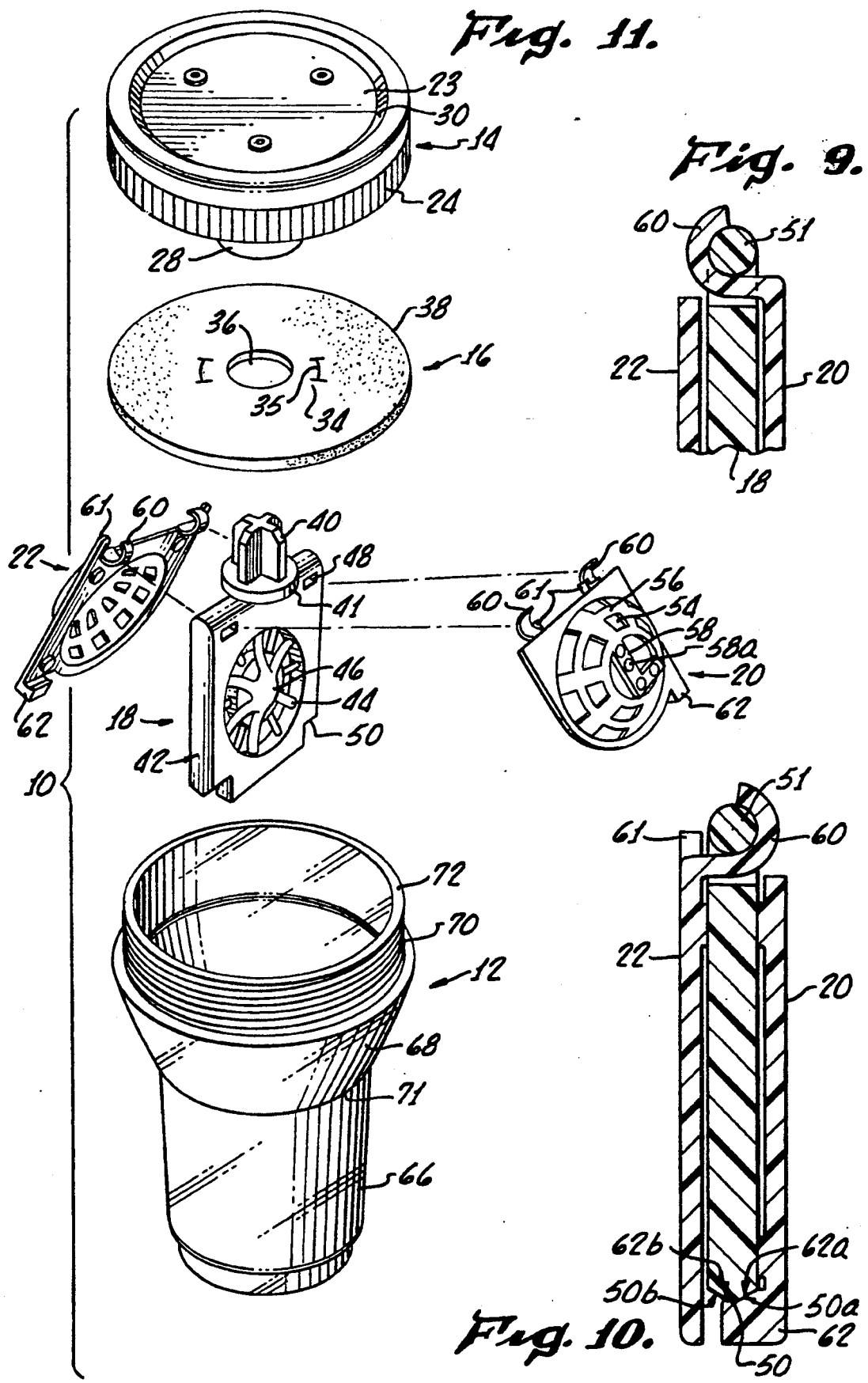

VENTED APPARATUS FOR STORING AND CLEANING AN ELEMENT

BACKGROUND OF THE INVENTION

1. Field of the Invention

The present invention generally relates to a vented container for storing and cleaning an element and, more specifically, to a vented container for the chemical disinfection of contact lenses which allows the pressure which develops during the chemical disinfection process to vent while preventing leakage of the cleaning solution.

2. Description of the Prior Art

In the past, the need to periodically disinfect and store contact lenses has been well known. Contact lenses can be disinfected through heat or through chemical disinfection. One type of chemical disinfection involves submerging the lenses in a 3% hydrogen peroxide solution which disinfects the lenses. After the lenses have been submerged for a prescribed period of time, a neutralizing tablet such as Oxysept ® which is manufactured by Allergan of Irvine, Calif., is added to the solution. A chemical reaction then occurs which neutralizes the hydrogen peroxide. As a byproduct of that reaction, oxygen gas is released.

Prior containers for chemical disinfection of contact lenses had the problems of allowing the disinfection solution to leak out of the container or permitting excessive pressure to build up within the container during the disinfection process. Excessive pressure buildup could cause the container to crack or possibly explode or the disinfecting solution could leak out of the container when the container was opened and the pressure was released.

SUMMARY OF THE INVENTION

It is an object of the present invention to provide a container for the storage and chemical disinfection of contact lenses which allows the pressure which builds up during the disinfection process to be released but does not allow the solution within the container to leak out.

It is a further object of the present invention to provide such a container which will not allow liquid to leak out even if the container is knocked over or placed upside down after the pressure has been vented.

The present invention is an apparatus for storing and cleaning an element such as a contact lens. The apparatus includes a fluid containing receptacle with an open top and a cap for removably closing off the receptacle's top. The cap has at least one opening or vent hole. An element retaining housing or a basket with keepers is removably disposed within the receptacle. The housing has openings therethrough which allow fluid to flow from outside the housing to the interior of the housing where an element can be retained. A resilient gasket is mounted in the receptacle adjacent the opening in the cap. The gasket incorporates a normally closed valve adapted to open upon a predetermined increase in pressure within the receptacle and to release that pressure through the valve and through the opening in the cap.

A more complete understanding of the apparatus for storing and cleaning an element in accordance with the present invention, as well as recognition of additional objects and advantages therefore, will be afforded to those skilled in the art from a consideration of the following detailed description and accompanying drawings of exemplary embodiments thereof.

BRIEF DESCRIPTION OF THE DRAWINGS

FIG. 1 is a partial cut-away vertical view of an apparatus for storing and cleaning an element in accordance with the teachings of the present invention;

FIG. 2 is a cut-away view of the present invention taken along line 2—2 of FIG. 1;

FIG. 7 is a cut-away view of the basket and keepers of the present invention taken along lines 7—7 of FIG. 1;

FIG. 8 is a view taken along line 8—8 of FIG. 7;

FIG. 9 is a detail view of the hinge assembly taken along line 9—9 of FIG. 8;

FIG. 10 is a view taken along line 10—10 of FIG. 8; and

FIG. 11 is an exploded view of the apparatus of FIG. 1.

DETAILED DESCRIPTION OF THE PREFERRED EMBODIMENT

Figure 3:
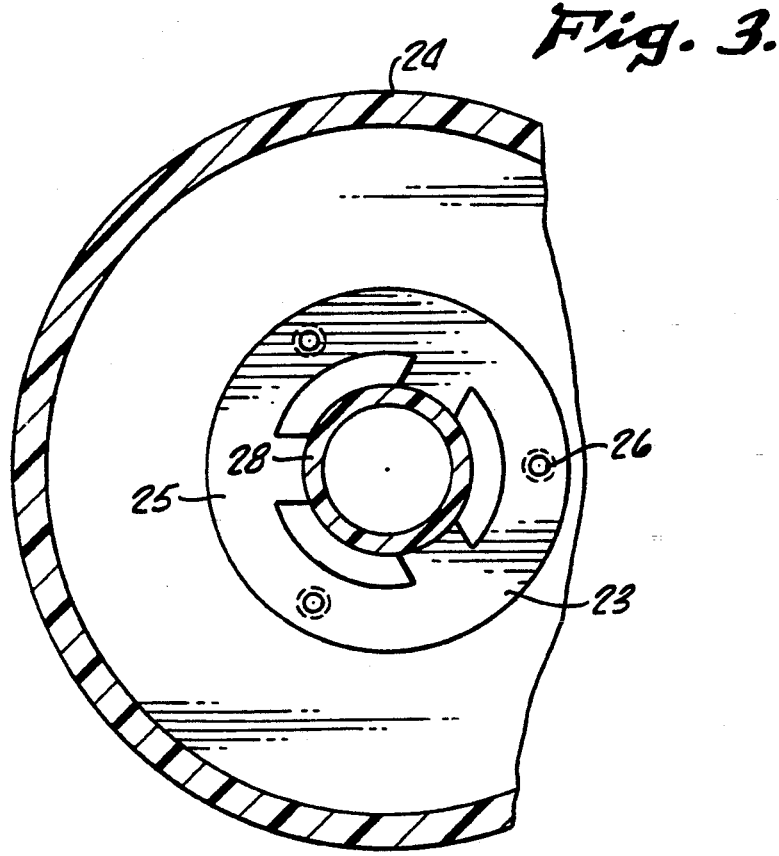
FIG. 3 is a cut-away view taken along line 3—3 of FIG. 1.

Referring now to the drawings, FIG. 11 shows an exploded view of a preferred embodiment of the apparatus for storing and cleaning an element indicated generally as 10. The apparatus incorporates a receptacle or vial 12, a cap 14, a gasket 16, a basket 18, a left keeper 20, and a right keeper 22. Unit 10 is shown assembled in a cross-sectional view in FIG. 1.

Cap 14, as can be seen in FIG. 1, includes a top piece 23 which is connected along its outside perimeter to a side wall 24. The cap 14 has a recessed annular groove 25 on its undersurface, most clearly shown in FIG. 1, which connects to vent holes 26 which extend through top piece 23 (FIG. 3). A cylindrical receptacle 28 is centrally located on the inner wall of the top piece 23, groove 25 surrounds the same (see FIG. 3). Edge 30 defines an indentation or shoulder on the upper surface of the cap 14. Sidewall 24 also includes internal threads 31 (see FIG. 1).

Figure 4:
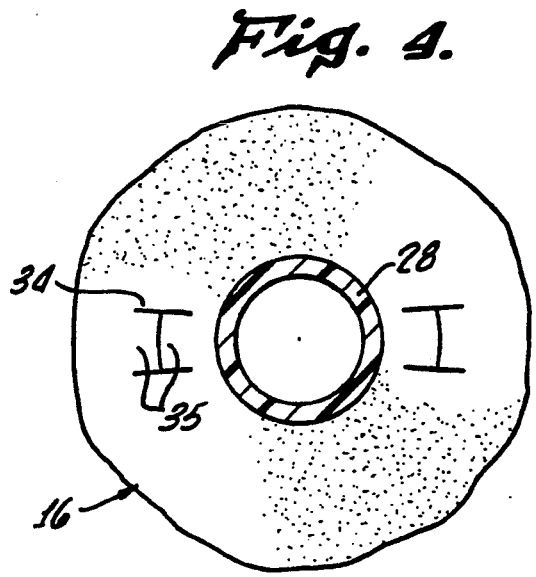
FIG. 4 is a detail cut-away view taken along line 4—4 of FIG. 1.

Gasket 16, as shown in FIG. 4, includes "H" shaped slits or perforations 34 extending therethrough on both sides of receptacle 28. The perforations 34, as can be seen in FIG. 1, are located in gasket 16 so as to be aligned with recessed groove 25 on cap 14. The perforations 34 are preferably "H" shaped and thereby form flaps 35. Gasket 16 has a perimeter 38 (FIG. 11) such that it fits snugly and securely within the side wall 24 of cap 14. Gasket 16 also includes receptacle opening 36 of a diameter such that it fits sealingly over receptacle 28 when gasket 16 is placed within cap 14 as shown in FIG. 2. The gasket is preferably made of an elastomeric material (preferably Dow Corning Silastic having a durometer reading of 55±5 Shore A ).

Basket 18 has a post 40 (FIG. 11) with an "X" shaped cross section which terminates in a stopper ring 41 shown in FIG. 11. Post 40 has an outside diameter equal to the inside diameter of receptacle 28 on cap 14. In a preferred embodiment, during assembly, the post 40 is inserted into the receptacle 28 until the stopper ring 41 abuts against the bottom of receptacle 28. The post is then ultrasonically welded to the inside of the receptacle 28. The gasket 16 is aligned and press fitted into the cap 14 prior to the attachment of the basket 18 to receptacle 28. The cap and the basket are preferably formed from a medical grade ABS resin polyac material.

Basket 18 further includes a main body portion 42. The central portion of body 42 is comprised of supporting ribs 44 with open spaces between them and left and right dome-shaped lens rests 46 (see FIG. 7). The body 42 further includes hinge openings 48 extending through the upper surface thereof (FIG. 11) and latch edges 50 which are formed by the junction of surfaces 50a and 50b at the bottom of body 42 as shown in FIG. 10. Cylindrical pivots 51, shown in FIGS. 9 and 10, are located above the hinge openings 48.

The left and right keepers 20 and 22 include a plurality of openings 54 which are defined by interconnected struts 56 (FIGS. 2 and 11). One strut is formed and marked in the shape of the letter "L" (FIG. 11) on the left keeper 20, indicated at 58, to indicate that the left contact lens should be placed in that side of the basket 18. Likewise, one strut on the right keeper 22 is formed in the shape of the letter "R" as indicated at 59, shown in FIG. 1, to indicate that the right contact lens should be placed in that side of the basket 18. The left keeper also has a series of raised bumps 58a on the "L" shaped strut so that the keepers can be differentiated by feel (FIG. 2). The keepers 20, 22 are also preferably made from a medical grade ABS resin polyac material. Other suitable medical grade plastics also may be used.

The keepers 20, 22 further include hinges 60 along with two retainers 61, which pass through hinge openings 48, as seen in FIGS. 8 and 9, and pivotally attach the keepers 20 and 22 to the pivot points 49 (see also FIG. 7). The hinges 60 are placed on the two keepers 20, 22 such that they do not interfere with the hinges of the other keeper. The keepers 20 and 22 each also include a snap latch 62 at the bottom thereof (FIG. 11) which can be firmly latched onto latch edges 50 (FIG. 10) and thereby securely hold the keepers 20, 22 in a closed position. Retaining edges 62a and 62b engage surfaces 50a and 50b respectively when the snap latch 62 is in the latched position (FIG. 10). The entire keeper provides sufficient flexibility to permit the latch 62 to move into and out of the latched position by the application of a small amount of force by a user.

The vial 12 (FIG. 1) has a flat bottom 64 so that the vial 12 may securely rest on a flat surface, such as a counter top. Cylindrical wall 66 extends perpendicularly from flat bottom 64 to a sloping wall 68. Fill line 71 (FIG. 11) may be inscribed at the junction of parallel wall 66 and sloping wall 68. Threaded lip 70 extends outward from sloping wall 68 and terminates in a stopped sealing edge 72 as shown in FIG. 1. Sealing edge 72 provides a pinch seal by pinching gasket 16 against the bottom surface of top piece 23 of cap 14 when cap 14 is firmly screwed into threaded lip 70 (FIG. 1). Vial 12 is of a depth sufficient to allow cap 14 to be screwed onto threaded lip 70 while still allowing sufficient room between basket 18 and flat bottom 64 for a typical chemical disinfecting tablet (see tablet 100 on FIG. 2) to rest. The vial 12 is preferably formed from a clear medical grade poly (methyl methylacrilic) acryrex material.

In operation, a user removes the cap 14 and its attached basket 18 and keepers 20 and 22 from the vial 12 and pours an amount of 3% hydrogen peroxide solution sufficient to fill the vial 12 to the line 71 while the vial 12 is resting on its flat bottom 64 on a flat surface. The user then places a right contact lens on the lens rest 46 on the side of the basket 18 with the right keeper 22 and then latches the right keeper 22. The user then places the left lens on the remaining lens rest 46 and latches the left keeper 20 over that lens. Then, the basket 18 is inserted into the vial 12, the cap 14 is screwed onto the vial and the lenses are thereby submerged in the solution. After a prescribed period of time, the cap is unscrewed and the user drops a neutralization tablet 100 (FIG. 2), such as an Oxysept ® or OmniCare ® tablet manufactured by Allergan into the vial 12 and rescrews the cap 14 onto the vial 12. The cap 14 should be screwed on tight enough to provide an airtight seal where the sealing edge 72 contacts the gasket 16. The side wall 24 may be knurled to assist in screwing cap 14 on or off of vial 12.

Figure 6:
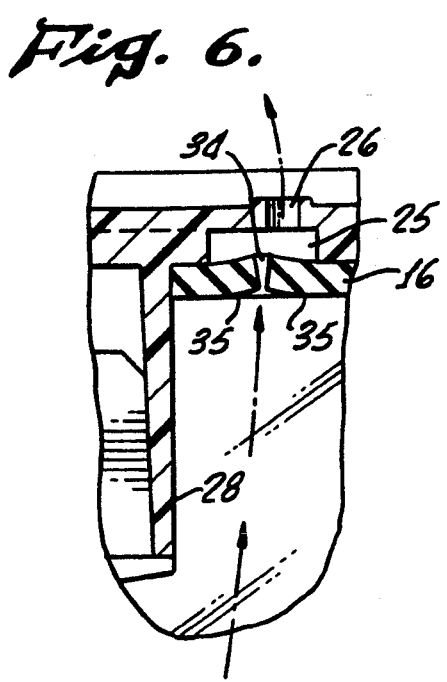
FIG. 6 illustrates the venting action of the valve assembly of the present invention.

When the cap 14 is screwed onto the vial 12, the portion of the basket 18 and keepers 20, 22 which contain the contact lenses are again submerged in the hydrogen peroxide solution as shown in FIG. 2. As the chemical neutralization process proceeds, oxygen gas is formed and the pressure within the container increases. When the pressure within the container reaches a predetermined level, the pressure forces the flaps 35 to deflect (FIG. 6) into the recessed groove 25 which allows the pressure to vent through the central slit, into the recessed groove 25, and out through the vent holes 26 as shown in FIG. 6. The level of pressure necessary to deflect the flaps 35 and allow the pressure to vent can be varied by altering the dimensions of the "H" shaped perforations. The venting pressure can also be varied by increasing or decreasing the stiffness of the gasket material.

Figure 5:
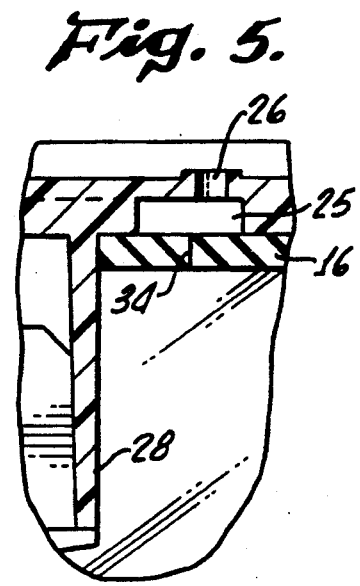
FIG. 5 is a detailed cut-away view of a valve used in the present invention.

As the pressure within the apparatus 10 decreases, the flaps 35 return to their normal sealed position shown in FIG. 5. When the flaps 35 are in their normal sealed position, the gasket 16 provides a liquid tight seal which will prevent any leakage of the solution in the apparatus 10 even if the apparatus 10 is turned upside down. If an especially vigorous reaction occurs within the apparatus 10 and some liquid is forced through the flaps during venting, that liquid will be contained within the recess defined by peripheral edge or shoulder 30.

Having thus described the exemplary embodiments of the present invention, it should be noted by those skilled in the art that the within disclosures are exemplary only and that various other alternatives, adaptations and modifications may be made within the scope of the present invention. Accordingly, the present invention is not limited to the specific embodiments as illustrated herein and is defined only by the following claims.

We claim:

1. A vented contact lens storage and cleaning container comprising:
   a container having a side wall, a bottom wall and an open top;
   a cap removably attached to said container and closing off said opening in said container, said cap having an upper surface and a lower surface, said cap having a recess in said lower surface and a vent hole located within said recess and extending through said cap;
   a gas and liquid impermeable gasket adjacent said vent hole in said cap including at least one "H"-shaped perforation extending therethrough which acts as a one way valve, said "H"-shaped perforation forming a pair of adjacent flaps which are normally closed and in abutting relationship forming a fluid-tight seal, said flaps being deflectable at sufficiently high pressure levels to move away from their normal closed position to permit gas to vent through said perforation and out of said vent hole and said caps thereby providing two hinged venting flaps allowing fast evacuation of gasses generated within said container; and basket means removably mounted in the interior of said container for removably containing contact lenses and allowing liquid to freely flow over the contact lenses.

2. The container of claim 1 wherein said perforations in said gasket are placed so as to be in alignment with said recess in said cap when said gasket forms a seal between said cap and said vial.

3. Apparatus for storing and disinfecting contact lenses comprising:
   a fluid containing vial having a sidewall, a bottom wall and an open top;
   a cap capable of engaging said vial including a top side and a bottom side, said bottom side having a recessed groove and at least one vent hole within said recessed groove;
   a basket attached to said bottom side of said cap for retaining at least one contact lens therein, said basket having at least one opening therethrough fluidly communicating the interior of said basket with the exterior thereof; and
   a vapor and liquid impermeable resilient gasket mounted adjacent said recessed groove, said gasket having at least one slit therethrough, said slot being "H"-shaped and forming a pair of adjacent flaps which are normally closed and in abutting relationship forming a fluid-tight seal, said flaps being deflectable at sufficiently high pressure levels to move away from their normal closed position to permit gas to vent through said slot and out of said vent hole and said cap thereby providing two hinged venting flaps allowing fast evacuation of gases generated within said vial.

4. In the apparatus of claim 3 wherein said cap includes a downward extending hollow receptacle on its bottom side, said basket including a part disposed in said receptacle retained therein.

5. In the apparatus of claim 4 wherein said basket further includes a central main body portion having a generally vertical front wall and a rear wall with through passages extending therethrough and a lens rest on each of said front and rear body portion walls for receiving a contact lens thereon, and a pair of keeper members removably attached to said main body portion on each of said front and rear body portion walls overlying said respective lens rests, each of said keeper members having through passages extending therethrough.

6. In the apparatus of claim 5 wherein said keeper members are snap fit to said main body portion.

7. In the apparatus of claim 6 wherein said keeper members are hinged at the top to said main body portion and snap fit to the bottom of said main body portion.

8. In the apparatus of claim 5 wherein said lens rests are dome shaped.

9. In the apparatus of claim 3 wherein said gasket is of silastic material.

10. In the apparatus of claim 9 wherein said silastic material has a durometer reading of about 55 Shore A.

11. In the apparatus of claim 9 wherein said silastic material is opaque.

* * * * *